(12) United States Patent
Auger et al.

(10) Patent No.: US 11,730,862 B2
(45) Date of Patent: Aug. 22, 2023

(54) IDENTIFIER-BASED APPLICATION OF THERAPEUTIC COATINGS TO MEDICAL IMPLANT DEVICES

(71) Applicant: DePuy Synthes Products, Inc., Raynham, MA (US)

(72) Inventors: Daniel D. Auger, Fort Wayne, IN (US); Rajendra K. Kasinath, Zionsville, IN (US); David A. B. Smith, North Webster, IN (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 16/869,782

(22) Filed: May 8, 2020

(65) Prior Publication Data

US 2021/0346575 A1 Nov. 11, 2021

(51) Int. Cl.
*A61L 27/54* (2006.01)
*A61L 27/28* (2006.01)
(Continued)

(52) U.S. Cl.
CPC .............. *A61L 27/54* (2013.01); *A61L 27/28* (2013.01); *G06K 19/07* (2013.01);
(Continued)

(58) Field of Classification Search
CPC ...... A61L 27/54; A61L 27/28; A61L 2420/02; G06K 19/07; G06K 19/0723; G16H 20/10; G16H 40/40
See application file for complete search history.

(56) References Cited

U.S. PATENT DOCUMENTS 6,814,490 B1  11/2004  Suhm et al.
7,175,081 B2   2/2007  Andreasson et al.
(Continued)

FOREIGN PATENT DOCUMENTS

CA         2716896 A1       9/2009
WO    WO-2020129124 A1 *    6/2020    ............. B05C 21/00

OTHER PUBLICATIONS

Federal Register, vol. 78, No. 185, Department of Health and Human Services, Food & Drug Administration, Part V, Unique Device Identification System; Final Rule, Sep. 24, 2013, Executive Summary section, pp. 58786-58787.
(Continued)

*Primary Examiner* — Thien M Le
*Assistant Examiner* — Asifa Habib
(74) *Attorney, Agent, or Firm* — BakerHostetler

(57) ABSTRACT

Techniques are provided for controlling delivery of a therapeutic coating to a medical implant device. An identifier of the medical implant device may be received. It may be determined, based at least in part on the first identifier, that the first medical implant device is approved to receive the therapeutic coating. A coating applicator system may be switched from a locked state in which it is prohibited from applying the therapeutic coating to an unlocked state in which it is permitted to apply the therapeutic coating. The coating applicator system may, while in the unlocked state, apply the therapeutic coating to the first medical implant device. After the applying of the therapeutic coating, the coating applicator system may be switched from the unlocked state back to the locked state.

20 Claims, 9 Drawing Sheets

(51) Int. Cl.
  *G06K 19/07* (2006.01)
  *G16H 20/10* (2018.01)
(52) U.S. Cl.
  CPC ...... *G06K 19/0723* (2013.01); *A61L 2420/02* (2013.01); *G16H 20/10* (2018.01)

(56) References Cited

U.S. PATENT DOCUMENTS

| | | | |
|---|---|---|---|
| 7,362,228 B2 | 4/2008 | Nycz et al. | |
| 7,421,367 B2 | 9/2008 | Nye | |
| 7,492,261 B2 | 2/2009 | Cambre et al. | |
| 7,639,136 B1 | 12/2009 | Wass et al. | |
| 7,753,272 B2 | 7/2010 | Harper et al. | |
| 8,113,425 B2 | 2/2012 | Dearing et al. | |
| 8,118,997 B2 | 2/2012 | Ebrom et al. | |
| 8,416,080 B2 | 4/2013 | Higham | |
| 8,668,742 B2 | 3/2014 | Caylor et al. | |
| RE46,582 E | 10/2017 | Morgan et al. | |
| 10,098,761 B2 | 10/2018 | Sherman et al. | |
| 10,194,802 B2 | 2/2019 | Windolf | |
| 10,363,102 B2 | 7/2019 | Abovitz et al. | |
| 2005/0283382 A1 | 12/2005 | Donoghue et al. | |
| 2006/0073265 A1* | 4/2006 | Teichman | A61F 2/82 427/2.1 |
| 2007/0135965 A1 | 6/2007 | Nguyen et al. | |
| 2008/0135733 A1 | 6/2008 | Feilkas et al. | |
| 2008/0157967 A1 | 7/2008 | Jones et al. | |
| 2008/0311281 A1* | 12/2008 | Andreacchi | B05B 15/55 118/712 |
| 2009/0021345 A1 | 1/2009 | Sriharto et al. | |
| 2009/0109033 A1 | 4/2009 | Salvat | |
| 2010/0136209 A1* | 6/2010 | Ou-Yang | C09D 5/14 427/2.1 |
| 2011/0039013 A1* | 2/2011 | Papp | B05B 16/20 118/500 |
| 2011/0276338 A1 | 11/2011 | Warner et al. | |
| 2012/0181200 A1 | 7/2012 | Hulliger | |
| 2012/0323597 A1 | 12/2012 | Woolford | |
| 2013/0087609 A1 | 4/2013 | Nichol et al. | |
| 2013/0245939 A1 | 9/2013 | Chang et al. | |
| 2013/0332323 A1* | 12/2013 | Phillips | G07C 9/22 705/28 |
| 2015/0173843 A1 | 6/2015 | Maughan et al. | |
| 2015/0174600 A1* | 6/2015 | Sim | B05B 12/08 235/376 |
| 2015/0347689 A1* | 12/2015 | Neagle | A61B 5/0836 705/3 |
| 2017/0103291 A1* | 4/2017 | Lolli | H05K 13/06 |
| 2019/0205724 A1* | 7/2019 | Roth | G06K 19/0723 |
| 2020/0171198 A1 | 6/2020 | Ou et al. | |
| 2020/0171209 A1 | 6/2020 | Cichocki et al. | |
| 2020/0171520 A1 | 6/2020 | Cichocki et al. | |
| 2020/0171528 A1 | 6/2020 | Cichocki et al. | |
| 2020/0172740 A1 | 6/2020 | Ou et al. | |
| 2021/0116892 A1* | 4/2021 | Bonzi | G05B 19/4183 |

OTHER PUBLICATIONS

U.S. Appl. No. 62/773,102, filed Nov. 29, 2018, Inventor Frank Cichocki, entitled Operating Room Coating Applicator.

* cited by examiner

IDENTIFIER-BASED APPLICATION OF THERAPEUTIC COATINGS TO MEDICAL IMPLANT DEVICES

TECHNICAL FIELD

The present disclosure relates generally to medical implant devices, and more particularly to application of therapeutic coatings to medical implant devices.

BACKGROUND

The embodiments disclosed herein are generally directed towards controlling application of therapeutic coatings to medical implant devices based on electronically-readable identifiers assigned to the medical implant devices.

Point-of-care coating applicators are used to apply various therapeutic coatings to medical implant devices, such as hip, knee and other joint implants. For example, an Operating Room Coating Applicator (ORCA) device may be used to apply therapeutic coatings to medical implant devices in an operating room setting. Some examples of therapeutic coatings may include anti-infective coatings, such as triclosan, or a pain prophylaxis medicament. Some coatings and implant treatments may have shelf-life limitations, may require specific storage-temperature ranges, or may require special sterilization methods. These and other issues may be alleviated through a point-of-care application.

Point-of-care applicators may sometimes be accidentally or intentionally misused, such as by applying an improper type of coating or an improper coating dosage to a medical implant device. For example, coatings may be improperly delivered to medical implant devices via off-label or other unauthorized applications. Coatings or coating dosages may sometimes be used that are incompatible with a particular patient, a particular implant type and/or size, or a particular geographic region or other physical environment. This misusage may result in various problems and complications, such as increased pain and discomfort, infection, and other potentially serious side-effects.

SUMMARY

In accordance with one embodiment, a method is provided for controlling delivery of a therapeutic coating to a first medical implant device. The method includes receiving a first identifier of the first medical implant device. The method further includes determining, based at least in part on the first identifier, that the first medical implant device is approved to receive the therapeutic coating. The method further includes, in response to the determining step, switching a coating applicator system from a locked state in which the coating applicator system is prohibited from applying the therapeutic coating to an unlocked state in which the coating applicator system is permitted to apply the therapeutic coating to the first medical implant device. The method further includes applying, by the coating applicator system, while in the unlocked state, the therapeutic coating to the first medical implant device.

A dosage amount of the therapeutic coating that may be approved for the first medical implant device may be determined, based at least in part on the first identifier, and the coating applicator system may be permitted to apply no more than the dosage amount of the therapeutic coating to the first medical implant device. Additionally, a selected type of the therapeutic coating that may be approved for the first medical implant device may be determined, based at least in part on the first identifier, and the coating applicator system may be permitted to apply only the selected type of the therapeutic coating to the first medical implant device.

The step of determining, based at least in part on the first identifier, that the first medical implant device is approved to receive the therapeutic coating may include comparing the first identifier to information indicating approved identifiers of approved medical implant devices that are approved to receive therapeutic coating delivery and confirming that the first identifier is included in the approved identifiers.

The first identifier may be removed from the approved identifiers based on the applying of the therapeutic coating to the first medical implant device. Additionally, after the applying of the therapeutic coating to the first medical implant device, the coating applicator system may be switched from the unlocked state back to the locked state.

In one embodiment, the first identifier may be read using an electronic reader. The electronic reader may be a radio-frequency identification (RFID) reader. The first identifier may be read from the first medical implant device. A packaging of the first medical implant device may shield the first medical implant device by preventing the reading of the first identifier from the first medical implant device while the first medical implant device is enclosed within the packaging. The electronic reader may be included in an applicator device of the coating applicator system and may be configured to read device identifiers in an interior area of the applicator device. Access to the interior area of the applicator device may be limited such that another medical implant device cannot be inserted into the interior area of the applicator device after the reading of the first identifier and prior to the applying of the therapeutic coating.

In one embodiment, the first identifier may be received via manual entry by a user. Additionally, a physical attribute of the first medical implant device may be sensed.

In one embodiment, the coating applicator system may comprise a base unit and a bag. The first medical implant device may be inserted into the bag. The base unit may provide an electrical connection for heating the bag and may cause an air vacuum to occur in bag. The heating of the bag and the air vacuum may result in the applying of the therapeutic coating to the first medical implant device.

In accordance with another embodiment, a computing system is provided for controlling delivery of a therapeutic coating to a first medical implant device. The computing system comprises one or more processors and one or more memories. The one or more memories have stored therein instructions that, upon execution by the one or more processors, cause the computing system to perform steps. The steps include receiving a first identifier of the first medical implant device. The steps further include determining, based at least in part on the first identifier, that the first medical implant device is approved to receive the therapeutic coating. The steps further include, in response to the determining step, switching a coating applicator system from a locked state in which the coating applicator system is prohibited from applying the therapeutic coating to an unlocked state in which the coating applicator system is permitted to apply the therapeutic coating to the first medical implant device. While in the unlocked state, the coating applicator system applies the therapeutic coating to the first medical implant device.

The one or more memories may have stored therein further instructions that, upon execution by the one or more processors, cause the computing system to perform an additional step of determining, based at least in part on the first identifier, a dosage amount of the therapeutic coating that may be approved for the first medical implant device. The coating applicator system may be permitted to apply no more than the dosage amount of the therapeutic coating to the first medical implant device.

The one or more memories may have stored therein further instructions that, upon execution by the one or more processors, cause the computing system to perform an additional step of determining, based at least in part on the first identifier, a selected type of the therapeutic coating that may be approved for the first medical implant device. The coating applicator system may be permitted to apply only the selected type of the therapeutic coating to the first medical implant device.

The instructions for performing the step of determining, based at least in part on the first identifier, that the first medical implant device is approved to receive the therapeutic coating may include instructions for comparing the first identifier to information indicating approved identifiers of approved medical implant devices that are approved to receive therapeutic coating delivery and confirming that the first identifier is included in the approved identifiers.

The first identifier may be received from an electronic reader that reads the first identifier. The electronic reader may be a radio-frequency identification (RFID) reader.

BRIEF DESCRIPTION OF THE DRAWINGS

For a more complete understanding of the principles disclosed herein, and the advantages thereof, reference is now made to the following descriptions taken in conjunction with the accompanying drawings, in which.

DETAILED DESCRIPTION

Figure 1:
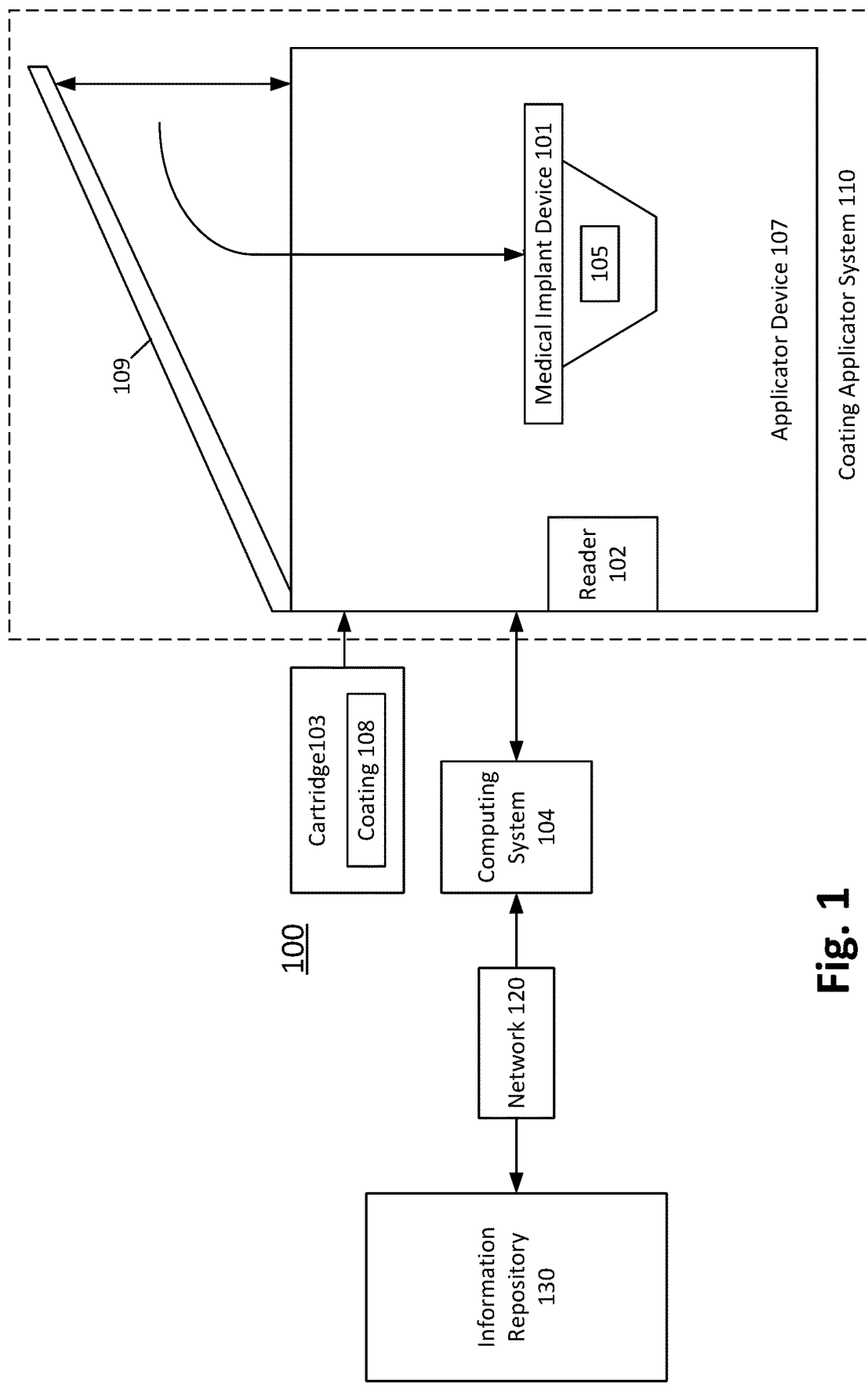
FIG. 1 is a diagram of an identifier-based therapeutic coating application control system in which a medical implant device is inserted into an applicator device.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims. Further, the term "at least one" stated structure as used herein can refer to either or both of a single one of the stated structure and a plurality of the stated structure. Additionally, reference herein to a singular "a," "an," or "the" applies with equal force and effect to a plurality unless otherwise indicated. Similarly, reference to a plurality herein applies with equal force and effect to the singular "a," "an," or "the"

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Generally, the techniques described herein relate to controlling delivery of therapeutic coatings to medical implant devices. An identifier of a medical implant device may be electronically read, for example, using a radio-frequency identification (RFID) reader, and the identifier may be used to determine whether the medical implant device is approved to receive a therapeutic coating. If the medical implant device is approved, a coating applicator system may be switched from a locked state, in which it is prohibited from applying any therapeutic coating, to an unlocked state, in which it is permitted to apply the therapeutic coating. The therapeutic coating may then be applied to the medical implant device while the coating applicator system is in the unlocked state. After applying of the therapeutic coating to the medical implant device, the coating applicator system may be switched from the unlocked state back to the locked state. It is noted, however, that the control techniques described herein are not necessarily limited to mere locking and unlocking of a system. For example, in one embodiment, the coating applicator system is unlocked with specific conditions, such as for only applying a specified coating type and/or coating dosage amount to a medical implant device. Additionally, different coating types and/or dosages may be employed for different patient, environmental, or other conditions. This may prevent misuse of the system by helping to ensure that improper coating types and/or dosages are not used.

In one embodiment, the system is only unlocked once for a particular medical implant device identifier, such as by indicating in centralized (e.g., cloud-based) stored records when a device has already been coated. This may prevent misuse of the system by helping to ensure that a single device identifier cannot be repeatedly used to coat multiple different devices. As another example, in one embodiment, the reader may be included within an applicator device and the range and directionality of the reader may be configured to only read identifiers from medical implant devices that have been inserted into an interior area of an applicator device, thereby helping to ensure that another medical device cannot be substituted for the medical implant device that is being read. In yet another example, in one embodiment, the packaging of a medical implant device may shield the device's identifier from being read from the device while it is still enclosed in its packaging, thereby also helping to ensure that another medical device cannot be substituted for the medical implant device that is being read. Specifically, it is prudent to use medical implant devices promptly after they are removed from their packaging, such as to prevent additional exposure to bacteria, germs, viruses and the like. It is submitted that these and other features described herein are tailored to provide advantages in the field of medical implant devices and, more specifically, to delivery of therapeutic coatings to medical implant devices at an operating room or other point-of-care location.

A coating applicator system, as that term is used herein, refers to an at least partially electrically-powered system that delivers therapeutic coatings, such as anti-infective coatings and analgesic coatings, to medical implant devices. A coating applicator system includes one or more at least partially electrically-powered components that cause and/or assist in coating delivery, such as heating components, air vacuum/pressure-lowering components, and the like. In some embodiments described herein, electrical power is used by the coating applicator system to provide power to components that cause heat to be applied to an area in which the therapeutic coating and/or a medical implant device is located, thereby allowing efficient application of the therapeutic coating to the medical implant device. Also, in some embodiments described herein, electrical power is used by the coating applicator system to provide power to vacuum-creating components that cause air to be removed from an area in which the therapeutic coating and/or a medical implant device is located, thereby allowing efficient application of the therapeutic coating to the medical implant device. In one example embodiment, such as described with reference to FIGS. 1-3 below, the applicator system includes an applicator device. The therapeutic coting is included in a cartridge and applied, by the applicator device, from the cartridge to the medical implant device. In another example embodiment, such as described with reference to FIG. 4 below, the applicator system includes both a base unit and a bag. The therapeutic coating and the medical implant device are enclosed in the bag. The base unit provides power to heat the bag. The base unit also removes air from the bag in order to create a vacuum in the bag. It is noted, however, that a coating applicator system is not limited to these example embodiments and may include other embodiments in which at least partially electrically-powered components or devices are employed to provide a coating to a medical implant device, such as electrically-powered sprayers, and the like.

Referring now to FIG. 1, a diagram of an identifier-based therapeutic coating application control system 100 corresponding to an embodiment will now be described in detail. As will be described in detail below, in the embodiments of FIGS. 1-3, a coating applicator system 110 includes an applicator device 107 that applies a coating 108 from a cartridge 103. In the illustrative embodiment of FIG. 1, a medical implant device 101 is inserted into an applicator device 107 that is configured to deliver the coating 108 to the medical implant device 101. In one embodiment, the medical implant device 101 is a joint implant device, such as a hip implant, a knee implant or another type of joint implant. The medical implant device 101 may also be any other type of medical implant device. The coating 108 is a therapeutic coating. In one embodiment, the coating 108 is an anti-infective, such as triclosan. In another embodiment, the coating 108 is an analgesic or a pain prophylaxis medicament. The coating 108 may also be any other type of coating suitable for use on a medical implant device. In one embodiment, the applicator device 107 is a point-of-care coating applicator that is used to apply the coating 108 at a location at which the medical implant device 101 is implanted into a patient. For example, the applicator device 107 may be an Operating Room Coating Applicator (ORCA) device that is used to apply the coating 108 at an operating room location.

The medical implant device 101 is assigned a device identifier. In one embodiment, the identifier may include numbers, letters, symbols and/or combinations thereof. In one embodiment, the device identifier is a unique identifier that is unique to the medical implant device 101. In another embodiment, the device identifier may be assigned to the medical implant device 101 and also to one or more other medical implant devices that share a common characteristic with the medical implant device 101, such as a common implant type, manufacturer, and the like. In the illustrated embodiment, the device identifier is electronically readable from an identification tag 105 of the medical implant device 101. In the illustrated embodiment, the applicator device 107 includes a reader 102, which is an electronic reader, such as a hardware device that is configured to electronically read the identification tag 105. In one embodiment, the identification tag 105 is a radio-frequency identification (RFID) tag, and the reader 102 is an RFID reader. In some examples, the identification tag 105 may be a passive RFID tag that does not require battery power in order to be read. This may be advantageous because it may allow the identification tag 105 to be read without requiring a battery to be included in the medical implant device 101. In other examples, however, the identification tag may be an active RFID tag that requires battery power in order to be read. In another embodiment, the identification tag 105 is a visual machine-readable tag, such as a bar code, and the reader 102 is a visual machine reader, such as a bar code reader. The identification tag 105 may also be any other type of tag that may be read electronically read, and the reader 102 may be any other type of electronic reader. In one embodiment, the identification tag 105 is embedded within the medical implant device 101. In another embodiment, the identification tag 105 is exposed on one or more surfaces of the medical implant device 101.

In another embodiment, an identification tag for the medical implant device 101 is additionally or alternatively located externally to the medical implant device 101, such as on a device packaging of the medical implant device 101 in which the medical implant device 101 may be enclosed prior to use. It is noted, however, that locating the identification tag 105 externally to the medical implant device 101 may potentially allow misuse of the system, such as by allowing the external identification tag to be read and then having a malicious user substitute another medical implant device for the medical implant device 101. By contrast, locating the identification tag 105 only on or within the medical implant device 101 may help to alleviate these concerns. Moreover, in one embodiment, the device packaging for the medical implant device 101 shields the medical implant device 101 by preventing electronic reading of the identification tag 105 while the medical implant device 101 is enclosed within the packaging. This may also be advantageous by allowing the identification tag 105 to be read only after the medical implant device 101 is removed from its packaging, thereby helping to alleviate the possibility that another device may be substituted for the medical implant device 101 after reading of the identification tag 105.

In the illustrated embodiment, the medical implant device 101 is inserted into the applicator device 107 by adjusting a cover 109 of the applicator device 107 to an open position in which the cover 109 is pulled away from the main body of the applicator device to expose an interior area of the applicator device 107 in which the coating 108 is applied. In another embodiment, the cover 109 may slide back and forth to expose an interior area of the applicator device 107. In the illustrated embodiment, the coating 108 is included in a cartridge 103, which may be inserted into the applicator device 107 by a user.

Figure 2:
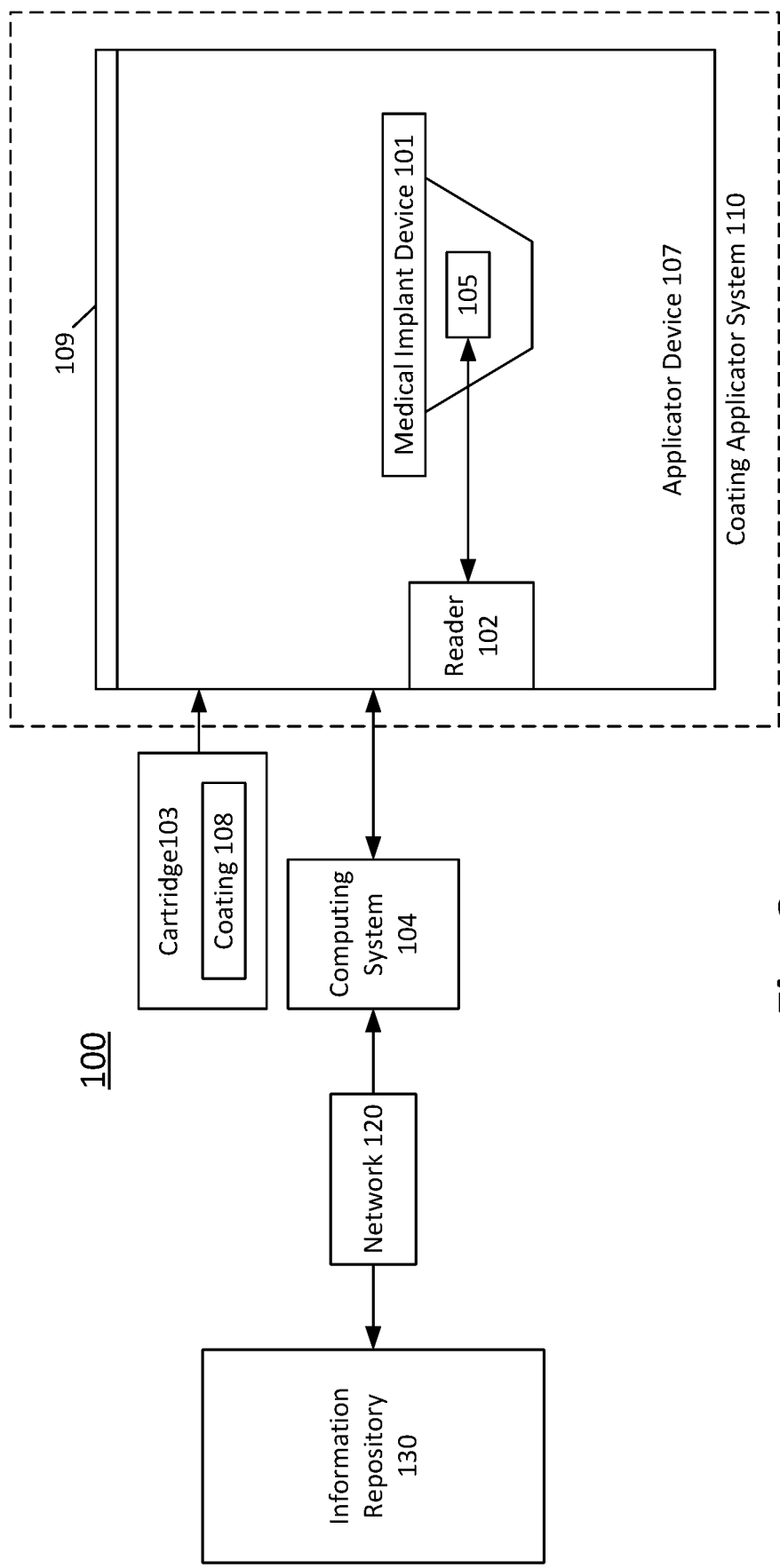
FIG. 2 is a diagram of an identifier-based therapeutic coating application control system in which an identifier of a medical implant device is read by a reader included in the applicator device.

Referring now to FIG. 2, an embodiment of control system 100 is illustrated in which the medical implant device 101 is inserted into the applicator device 107 and the cover 109 of the applicator device 107 has been adjusted to a closed position. In the illustrated embodiment, in the closed position, the cover 109 is pushed back towards the main body of the applicator device 107 to block access to the interior area of the applicator device 107.

In the illustrated embodiment of FIG. 2, the identification tag 105 of the medical implant device 101 is read by the reader 102. In one embodiment, the reading of the identification tag 105 may be performed automatically upon closing of the cover 109. In another embodiment, the reading of the identification tag 105 is manually requested, such as by pressing a button or other control that may be included on the applicator device 107. In the illustrated embodiment, the reader 102 is included in the applicator device 107. Inclusion of the reader 102 in the applicator device 107 may be advantageous, such as by reducing the possibility that another medical implant device can be inserted into the applicator device 107 and substituted for the medical implant device after reading of the identification tag 105. Moreover, in one embodiment, to further reduce the likelihood of misuse, the reader 102 is configured to only read identification tags that are located within an interior area of the of the applicator device 107. For example, a directionality and/or a distance range of the reader 102 may be configured such that the reader 102 can only read identification tags within an interior area of the applicator device 107 (i.e., such that the reader 102 cannot read identification tags that are external to the applicator device 107). Additionally, in one embodiment, to also further reduce the likelihood of misuse, the reader 102 is configured to only read identification tags when the cover 109 of the applicator device is closed or when access to an interior area of the applicator device is otherwise blocked or restricted. To yet further reduce the likelihood of misuse, access to the interior area of the applicator device 107 may be limited such that another medical implant device cannot be inserted into the interior area of the applicator device 107 after the reading of the identifier of the medical implant device 101 and prior to applying of the coating 108 to medical implant device 101.

Upon reading of the identification tag 105, the device identifier of the medical implant device may be identified by the reader 102 and provided to a computing system 104. In one embodiment, the computing system 104 is responsible for controlling operation of the coating applicator system 110 including applicator device 107. In one embodiment, the computing system 104 switches the coating applicator system 110 between a locked state and an unlocked state. In the locked state, the coating applicator system 110 is prohibited from applying any therapeutic coating. By contrast, in the unlocked state, the coating applicator system 110 is permitted to apply therapeutic coatings to medical implant devices that are approved to receive the therapeutic coatings. In one embodiment, the computing system 104 switches the coating applicator system 110 from the locked state to the unlocked state based on the device identifier of the medical implant device, thereby allowing a coating 108 to be delivered to the medical implant device 101. The computing system 104 may be located at the same point-of-care location (e.g., operating room) as the coating applicator system 110. In one embodiment, the computing system 104 may be wholly or partially included in the coating applicator system 110. For example, the computing system 104 may be wholly or partially included in applicator device 107 of FIGS. 1-3 or base unit 401 of FIG. 4. Thus, in some examples, operations described herein as being performed by computing system 104 may also be performed by coating applicator system 110, while operations described herein as being performed by coating applicator system 110 may also be performed by computing system 104. In one embodiment, the coating applicator system 110 may itself include computing components (e.g., processing components, memory components, etc.) in addition to those included in the computing system 104 (and described in greater detail below). The computing system 104 may have a connection to the coating applicator system 110 (or to components within the coating applicator system 110), such as a wired or wireless (e.g., local area network (LAN)) connection. This connection may allow the computing system 104 to send instructions to (or otherwise control) the coating applicator system 110 (or components within the coating applicator system 110). This connection may also allow instructions to be sent from portions of computing system 104 that may be external to the applicator device 107 or base unit 401 (or other components of the coating applicator system 110) to portions of the computing system 104 that may be included in the applicator device 107 or base unit 401 (or other components of the coating applicator system 110).

Figure 3:
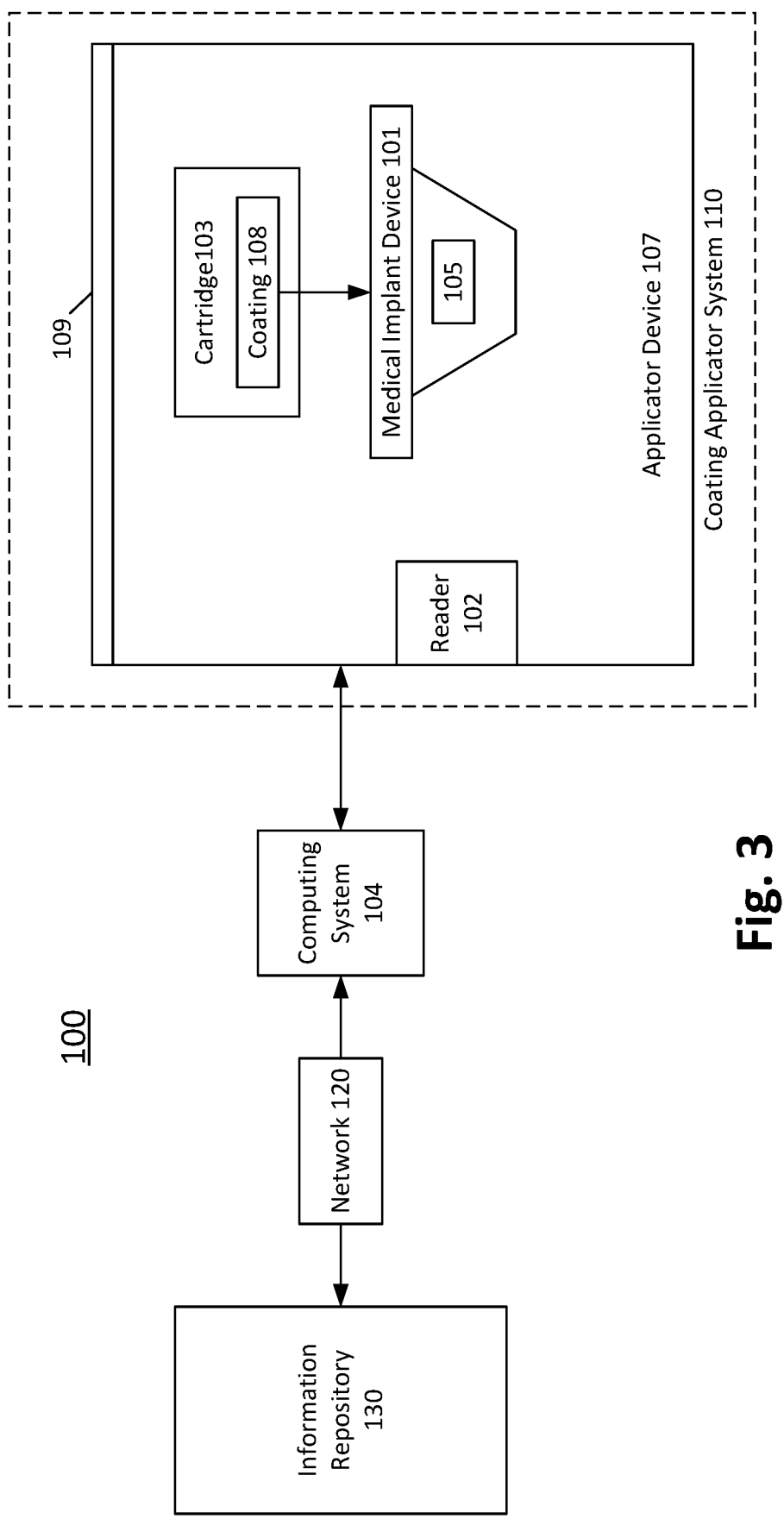
FIG. 3 is a diagram of an identifier-based therapeutic coating application control system in which a coating is applied to a medical implant device from a cartridge.

In one embodiment, the computing system 104 communicates with an information repository 130, such as a database, over a network 120. The network 120 may be a local area network (LAN) and/or a wide area network (WAN), such as the Internet. In one embodiment, the information repository 130 may be wholly or partially stored and updated using one or more cloud computing or other centralized computing services. As described in detail below, the information repository 130 may include approved device identifiers for medical implant devices that are approved to receive therapeutic coating delivery, and the computing system 104 may match the device identifier of the medical implant device 101 to one of the approved device identifiers. Referring now to FIG. 3, an embodiment of control system 100 is shown in which a coating 108 is applied to the medical implant device 101 by the applicator device 107 from cartridge 103. The applicator device 107 may cause the coating 108 to be applied to the medical implant device 101 by heating the coating 108 and lowering pressure within the interior area of the applicator device 107, thereby causing the coating 108 to be delivered to the medical implant device 101. In one embodiment, the coating 108 is applied upon confirming, based on the device identifier of the medical implant device 101, that the medical implant device is approved to receive the coating 108.

Figure 4:
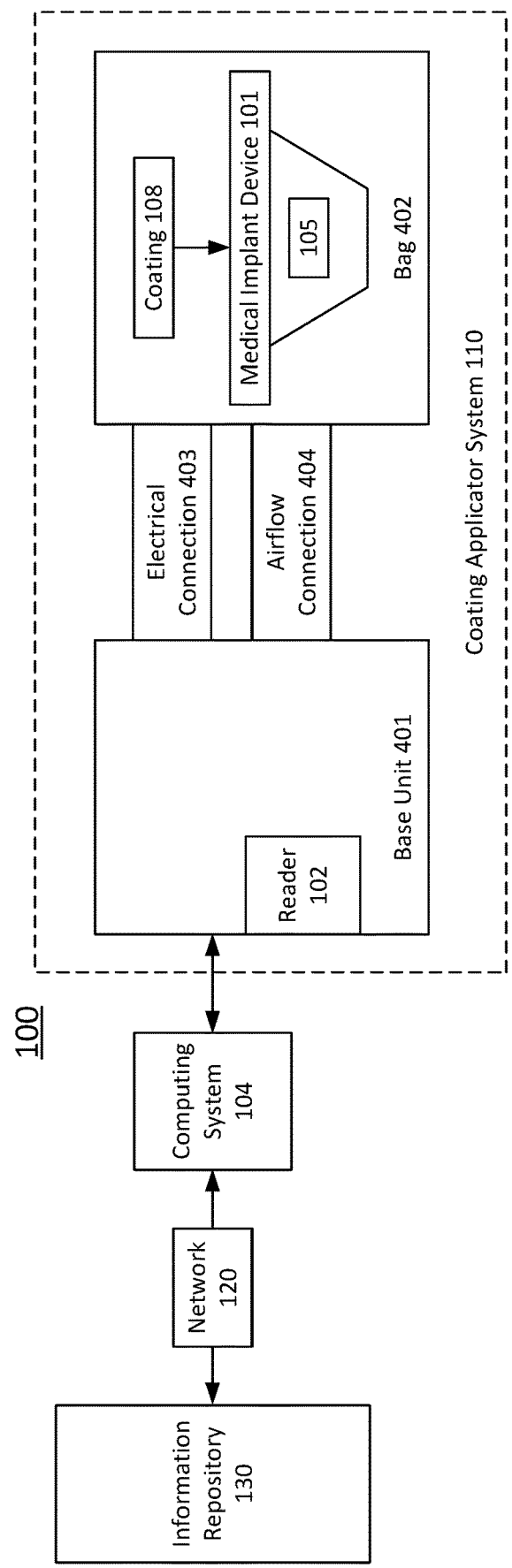
FIG. 4 is a diagram of an identifier-based therapeutic coating application control system in which a coating is applied to a medical implant device from a bag.

As described above, FIGS. 1-3 illustrate embodiments in which the coating applicator system 110 includes an applicator device 107 that that applies the coating 108 from a cartridge 103. As described above, the applicator device 107 may include heating components to heat the coating from the cartridge 103. The applicator device 107 may also create an environment of lowered pressure. The coating may be volatized under temperature (electrical heating) and lowered pressure and may coat parts in an interior area/chamber of the applicator device 107. It is noted, however, that a variety of different systems for applying of the coating may be employed in combination with the identifier-based control techniques described herein. In particular, FIG. 4 illustrates an alternative embodiment of control system 100 in which the coating applicator system 110 includes a base unit 401 and a bag 402 into which the medical implant device 101 is inserted for application of the coating 108. Specifically, the bag 402 may be opened and closed by a seal, such as a zipper-operated seal. The medical implant device 101 may be inserted into, and enclosed within, the bag 402 in order to apply the coating 108. In one embodiment, the bag 402 may include the coating 108 compounded into a conductive aluminum mesh and sandwiched within a top and bottom polymer mesh. In the illustrated embodiment, the bag 402 includes two connections to the base unit 401: an electrical connection 403 and an airflow connection 404. The base unit 401 provides the electrical connection 403 for heating the bag 402. Specifically, the electrical connection 403 provides power that, via the conductive aluminum mesh, causes the bag 402 to heat the coating 108. Additionally, the base unit 401 causes an air vacuum to occur in the bag 402. Specifically, the base unit 401 extracts air from the bag 402 via the airflow connection 404, thereby causing a vacuum within the bag 402. The heating of the bag 402 in combination with the air vacuum results in the coating 108 being applied to the medical implant device 101. The identifier of the medical implant device 101 may be read by reader 102, for example from identifier tag 105. As described in detail below, if the medical implant device 101 is approved, based on the device identifier, to receive a therapeutic coating, then the coating applicator system 110 may be unlocked to allow the base unit 401 to provide power to the bag 402 and to cause the vacuum in the bag 402, thereby resulting in delivery of the coating 108 to the medical implant device 101.

Figure 5:
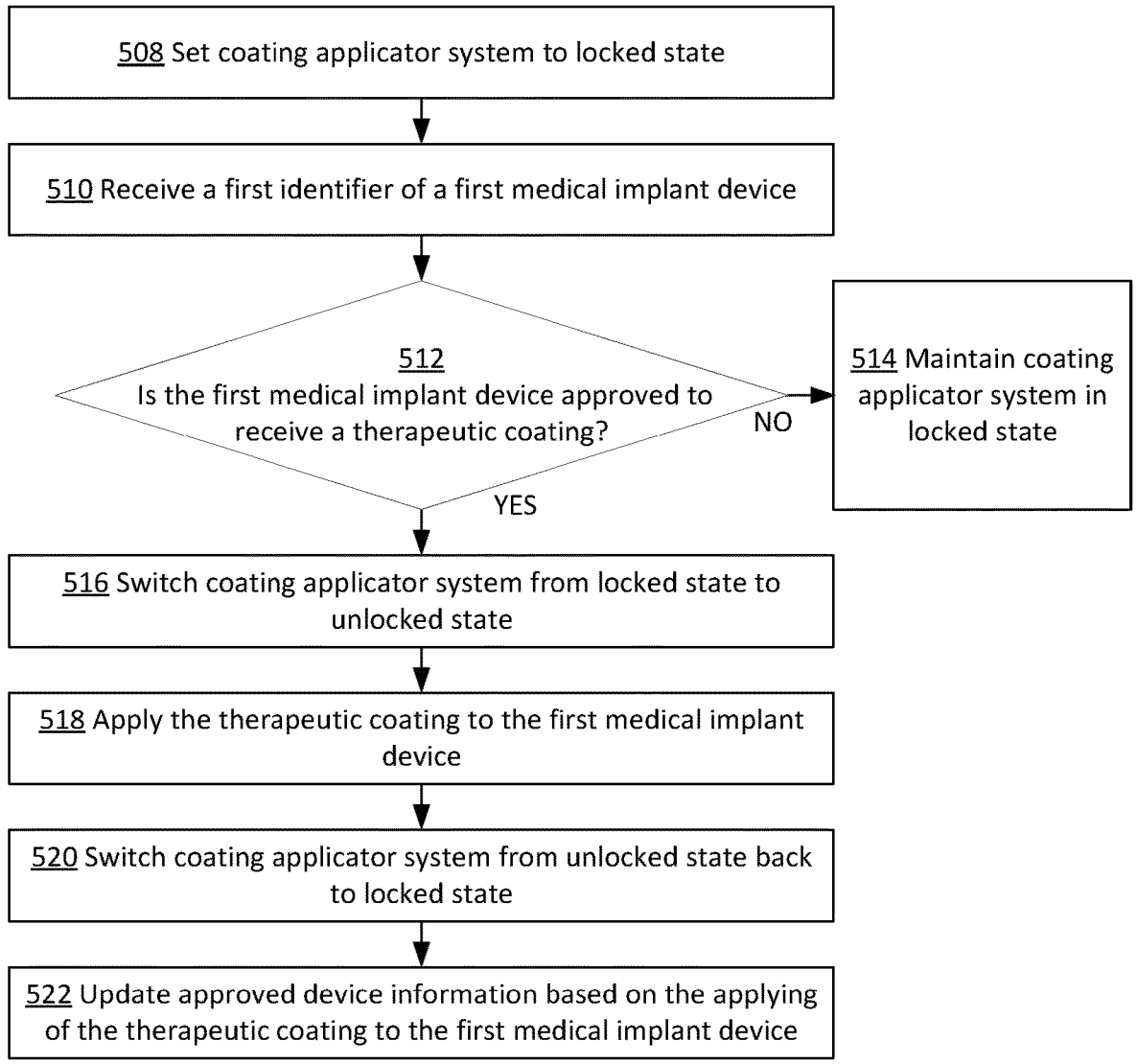
FIG. 5 is a flowchart illustrating steps of one embodiment of a method for controlling delivery of a therapeutic coating to a medical implant device.

Referring now to FIG. 5, one embodiment of a method for controlling delivery of a therapeutic coating to a medical implant device will now be described in detail. The method of FIG. 5 is initiated at operation 508, at which a coating applicator system is set to a locked state in which the coating applicator system is prohibited from applying a therapeutic coating to medical implant devices. It is noted that operation 508 need not necessarily be performed every time, as the coating applicator system may sometimes arrive to the hospital or other point-of-care location in the locked state. Additionally, it is noted that the coating applicator system may also be set to the locked state based on a prior performance of the process of FIG. 5, which may include switching the coating applicator back to a locked state after applying of a therapeutic coating (see operation 520 described below). The computing system 104 may set the coating applicator system to the locked state. In one embodiment, the computing system 104 may set the coating applicator system to the locked state by powering-off one or more components (e.g., applicator device 107 or base unit 401) of the coating applicator system. In one embodiment, the computing system 104 may control the supply of power to coating applicator system components and may restrict the supply of power to these components. For example, the computing system 104 may control a switch that may be opened to restrict the supply of power to the coating applicator system components or that may be closed to allow the supply of power to the coating applicator system components. In one embodiment, the computing system 104 sets the coating applicator system to a locked state by sending instructions to the coating applicator system to not perform coating delivery or to otherwise assume the locked state. These instructions may take the form of an electrical pulse or signal that is sent from the controller 104 to the applicator device 107 or the base unit 401 and/or a message that is sent via a local area network (LAN) or another communications medium. In one embodiment, the computing system 104 may send instructions to the coating applicator system to power itself off. For example, the controller 104 may send instructions to applicator device 107 or base unit 401 to power itself off. In an alternative embodiment, the applicator device 107, base unit 401, and/or other components of the coating applicator system may be powered-on when in the locked state, but the coating applicator system may nevertheless be prohibited from applying a therapeutic coating when in the locked state. For example, in one embodiment, one or more components of the coating applicator system are powered-on when in the locked state, but those components are programmed, or otherwise configured, to not allow coating delivery while in the locked state. In one embodiment, the computing system 104 may set the coating applicator system to the locked state by sending the coating applicator system instructions to not perform coating delivery. Additionally, in one embodiment, the computing system 104 may set the coating applicator system to the locked state by sending the coating applicator system instructions to assume the locked state, and instructions for not allowing coating delivery while in the locked state may be stored in memory components that may optionally be included in, or otherwise accessible to, the coating applicator system. In one embodiment, the coating applicator system is configured to operate in the locked state by default, and the coating applicator system is configured to switch to the unlocked state (and allow application of a therapeutic coating) only when explicitly instructed by the computing system 104 to do so.

At operation 510, a first identifier of a first medical implant device is received. The first identifier may be received by the computing system 104. In some embodiments, such as those shown in FIGS. 1-4, the computing system 104 may receive the first identifier from an electronic reader that reads the first identifier and then provides the first identifier to the computing system 104. For example, reader 102 may read a device identifier from an identification tag 105 of a medical implant device 101. As described, above, the device identifier may be read from the medical implant device, such as from an identification tag that is embedded into the first medical implant device or on one or more surfaces of the medical implant device. To prevent misuse, the electronic reader may be located at the same point-of-care location as the coating applicator system, such as in the same operating room as the coating applicator system. The computing system 104 may have a connection to the reader 102, such as a wired or wireless connection. This connection may allow the computing system 104 to receive information, such as signals, from the reader 102, and this information may indicate the first identifier of the first medical implant device as well as other identifiers or information.

In an alternative embodiment, as opposed to receiving the first identifier from an electronic reader, the computing system 104 instead receives the first identifier via manual entry by a user, such as by having the user type or otherwise enter the first identifier into a keyboard, keypad, or other user input component that may be included in the computing system 104.

Additionally, in one embodiment, the computing system 104 receives input from a sensor that may be employed to detect a physical attribute of the first medical implant device. The detected physical attribute may include size, shape, weight or any other suitable physical attribute of the first medical implant device. In one embodiment, the sensor is a scale (e.g., load cell sensor) that is configured to detect a weight of the first medical implant device. In another embodiment, the sensor is an optical and/or light-detecting sensor that is configured to detect a size and/or shape of the first medical implant, such as based on the presence or absence of light emitted from a source. The sensor may be located at the same point-of-care location as the coating applicator system, such as in the same operating room as the coating applicator system. The sensor may determine the physical attribute of the first medical implant device and then provide an indication of the physical attribute to the computing system 104. The computing system 104 may have a connection to the sensor, such as a wired or wireless connection. This connection may allow the computing system 104 to receive information, such as signals, from the sensor, and this information may indicate the physical attribute of the first medical implant device as well as other information. The computing system 104 may then use the indicated physical attribute as information to assist in confirming that the first medical implant device is, in fact, present at the same point-of-care location (e.g., operating room) as the coating applicator system. For example, information regarding physical attributes of the first medical implant device (e.g., size shape, weight, etc.) may be stored in combination with the first identifier of the first medical implant device. The computing system 104 may obtain this physical attribute information based on the first identifier and may attempt to match the physical attribute information indicated by the sensor with the stored physical attribute information obtained via the first identifier. If the indicated physical attribute information from the sensor matches the stored physical attribute information, then this may assist in confirming that the first medical implant device is, in fact, present at the same point-of-care location as the coating applicator system, and the process may continue to operation 512 as described below. By contrast, if the indicated physical attribute information from the sensor does not match the stored physical attribute information, then this may indicate that the first medical implant device is not present at the same point-of-care location as the coating applicator system, and unlocking of the coating applicator system may not be permitted. Because it assists in confirming the location of the first medical implant device, this physical attribute-based confirmation process may be particularly advantageous for scenarios in which the device identifier is not electronically read from the first medical implant device, such as when the first identifier is manually input into the computing system 104 by a user.

In one embodiment, a sensor may be used to prevent a user from attempting to coat multiple unauthorized implant devices per coating cycle. For example, a user may attempt to coat unauthorized implant devices by having a reader scan a single authorized implant device, but the user may then maliciously insert one or more unauthorized devices (in addition or as an alternative to the authorized device) into coating applicator system components such as a bag 402 or an interior coating area/chamber of the applicator device 107. In one embodiment, a sensor may be positioned at a suitable location (e.g., at the bag 402 or an interior coating area/chamber of the applicator device 107) to detect physical attributes of the medical implant device. As described above, this physical attribute information may then be sent to the computing system 104 to compare the indicated physical attribute information from the sensor to stored physical attribute information for the received device identifier. Unlocking of the coating applicator system may be permitted only when the indicated and stored information match one another. It is noted that an exact match may not be required, and the match may only need to be within a configurable range of similarity. In one specific example, a scale (e.g., load cell sensor) may be located at the bag 402 to measure a weight of the medical implant devices in the bag 402. If the measured weight exceeds the stored weight of the received device identifier, then this may indicate that one or more additional unauthorized implant devices have been inserted into the bag 402, and the unlocking of the coating applicator system may not be permitted. It is noted that many other example techniques are also described herein to assist in preventing against coating of unauthorized devices, and any number of these techniques may optionally be employed in combination with one another.

At operation 512, it is determined whether the first medical implant device is approved to receive a therapeutic coating. As described above, this determination may be made based at least in part on the first identifier of the first medical implant device. Specifically, when the first identifier is electronically read from the first medical implant device, the reader 102 may provide the first identifier to a computing system 104. The computing system 104 may then determine, based at least in part on the first identifier, whether the first medical implant device is approved to receive a therapeutic coating. In one embodiment, the computing system 104 may access information indicating approved device identifiers of approved medical implant devices that are approved to receive therapeutic coating delivery. As shown in FIGS. 1-4, this information may be stored in an information repository 130 external to the coating applicator system 110 and accessible via a network 120. In one embodiment, the computing system 104 may compare the first identifier of the first medical implant device to the approved device identifiers. If the first identifier is included in the approved device identifiers, then the computing system 104 may determine that the first medical implant device is approved to receive a therapeutic coating. By contrast, if the first identifier is not included in the approved device identifiers, then the computing system 104 may determine that the first medical implant device is not approved to receive the therapeutic coating. In one embodiment, the information also includes, for each approved medical implant device, an approved type of therapeutic coating for the approved medical implant device, such as an anti-infective (e.g., triclosan, etc.), an analgesic or a pain prophylaxis medicament, or another type of therapeutic coating. Additionally, in one embodiment, the information also includes, for each approved medical implant device, an approved dosage amount for the approved medical implant device.

The remote storage and accessing of approved device information at an information repository 130 over a network 120 may provide a number of advantages. For example, this configuration may allow the approved device information to be accessed and/or updated by any number of computing systems, applicator devices, manufacturer systems, and/or other components or devices spread across any number of locations and geographic areas. For example, this configuration may allow device manufacturers or other users to easily add new device identifiers to a list of approved device identifiers, such as when new medical implant devices are sold or otherwise made available for use. Additionally, in one embodiment, when an approved coating is applied to an approved medical implant device (and the device is implanted into a patient), the device's identifier may be removed from a list of approved medical devices. This may help to prevent misuse, such as by preventing a device identifier from being re-used to apply additional coatings to other unauthorized devices. The use of a network-accessible information repository 130 may, upon coating and implantation of a medical implant device, allow a computing system to easily remove the device's identifier from a list of approved medical device identifiers. Although the use of a network-accessible information repository may provide a number of advantages, it is not required. In an alternative embodiment, information indicating that a device is approved to receive a coating, as well as optionally a particular type and/or dosage of the coating, may be embedded into the device's identification tag.

Figure 6:
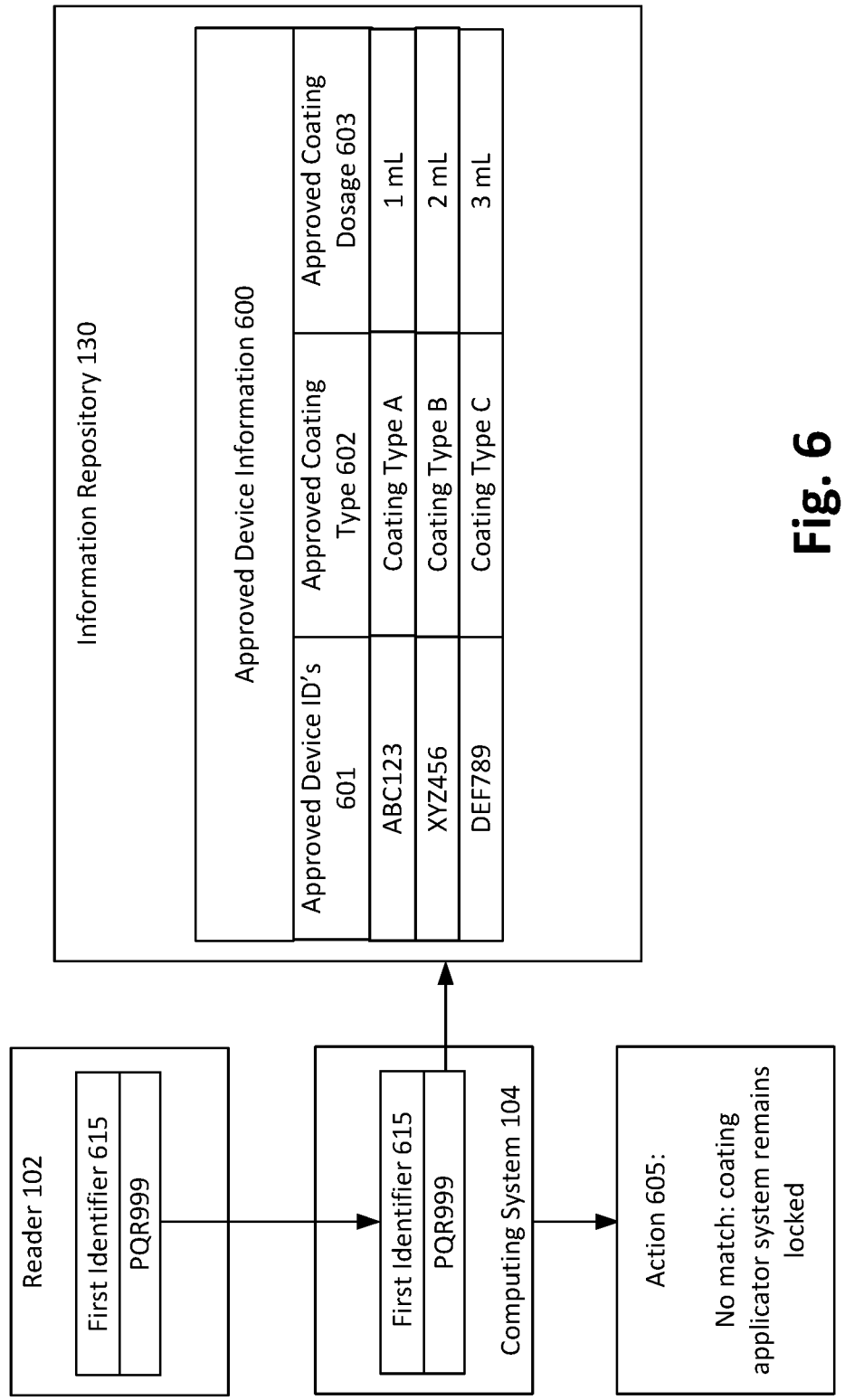
FIG. 6 is a diagram illustrating an example failed identifier match attempt for authorizing application of a therapeutic coating to a medical implant device.

When, at operation 512, it is determined that the first medical device is not approved to receive a therapeutic coating, then, at operation 514, in response to this determination, the coating applicator system is maintained in the locked state in which the coating applicator system is prohibited from applying a therapeutic coating. In one embodiment, the maintaining of the coating applicator system in the locked state is performed in response to determining, based at least in part on the first identifier, that the first medical implant device is not approved to receive a therapeutic coating. Specifically, it may be determined, based at least in part on the first identifier of the of the first medical implant device, that the first medical implant device is not approved to receive the therapeutic coating. This determination may include comparing the first identifier to information indicating approved identifiers of approved medical implant devices that are approved to receive therapeutic coating delivery and determining that the first identifier is not included in the approved identifiers. Referring now to FIG. 6, an example failed identifier match attempt for authorizing application of a therapeutic coating to a medical implant device will now be described in detail. In the illustrated embodiment, the reader 102 reads the first identifier 615 from the first medical implant device and provides the first identifier 615 to the computing system 104. As shown, in this example, the first identifier 615 is PQR999. The computing system 104 may then access approved device information 600 stored in information repository 130. In the illustrated embodiment, the approved device information 600 includes an approved device identifiers (IDs) column 601, which lists an identifier for each medical implant device that is approved to receive a therapeutic coating. As shown, in this example, there are three identifiers (ABC123, XYZ456, and DEF798) corresponding to three medical implant devices that are approved to receive a therapeutic coating. The approved device information 600 also includes an approved coating type column 602, which lists an approved coating type (Coating Type A, Coating Type B, Coating Type C) for each approved medical implant device. Coating Types A-C may be any different types of therapeutic coatings, such as analgesics, anti-infectives, and the like. In one specific example, Coating Type A could be a could be a specific type of analgesic, Coating Type B could be a specific type of anti-infective (e.g., triclosan), and Coating Type C could be another specific type of anti-infective. The approved device information 600 also includes an approved coating dosage column 603, which lists an approved coating dosage amount (1 milliliter (mL), 2 mL, 3 mL) for each approved medical implant device.

In the illustrated embodiment, the computing system 104 compares the first identifier 615 (PQR999) to the approved identifiers listed in the approved device IDs column 601 to attempt to match the first identifier 615 to one of the approved device identifiers. As shown, in this example, the first identifier 615 (PQR999) is not one of the three identifiers included in the approved device IDs column 601. Accordingly, in this example, as indicated at action 605, the computing system is unable to match the first identifier 615 (PQR999) to an approved device identifier, and the coating applicator system therefore remains in a locked state in which it is prohibited from applying a therapeutic coating to the first medical implant device.

Figure 7:
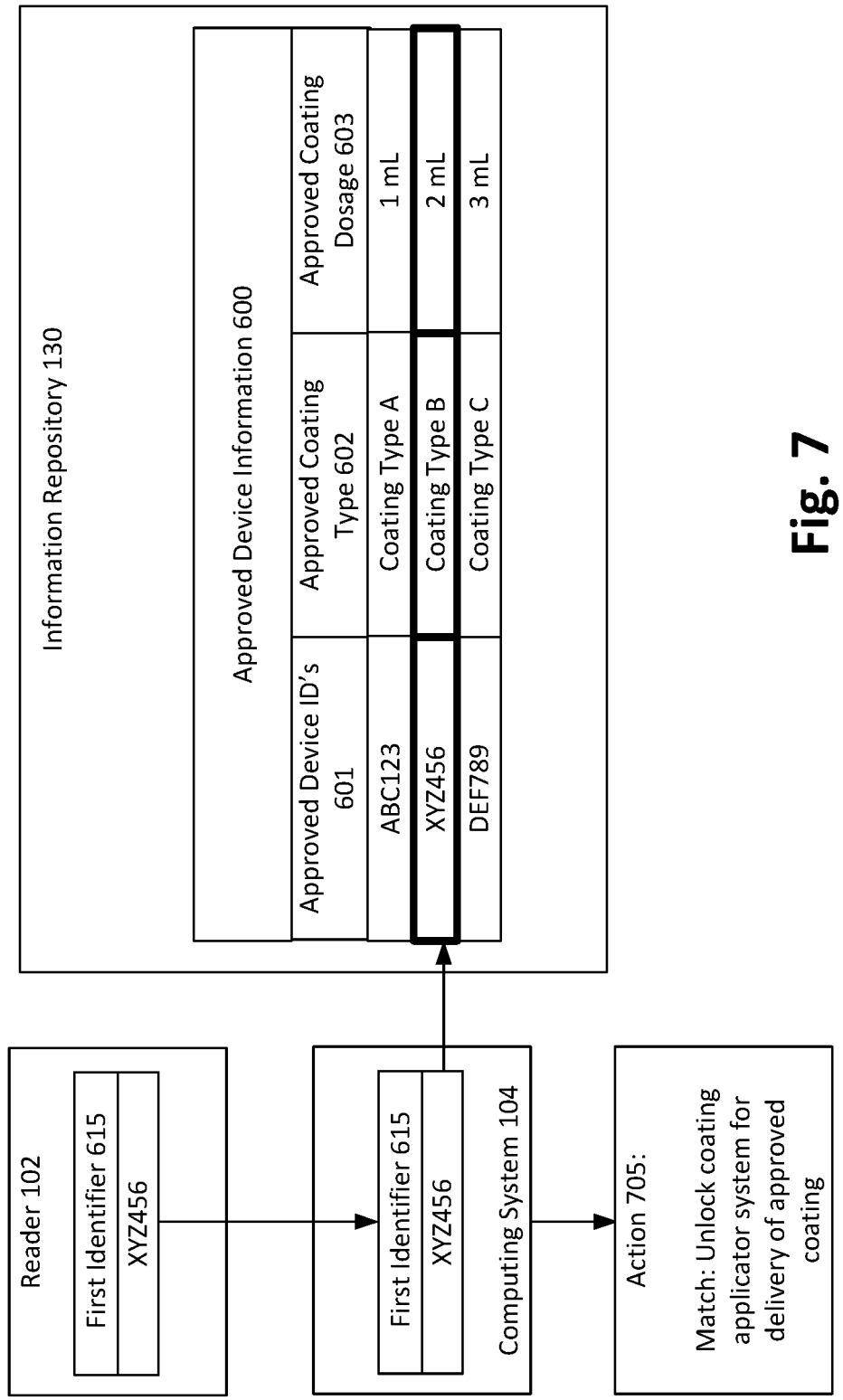
FIG. 7 is a diagram illustrating an example successful identifier match attempt for authorizing application of a therapeutic coating to a medical implant device.

Referring back to FIG. 5, when, at operation 512, it is determined that the first medical implant device is approved to receive a therapeutic coating, then, at operation 516, the coating applicator system is switched from the locked state, in which the coating applicator system is prohibited from applying the therapeutic coating, to an unlocked state, in which it is permitted to apply the therapeutic coating. In one embodiment, the switching of the coating applicator system from the locked state to the unlocked state is performed in response to determining, based at least in part on the first identifier, that the first medical implant device is approved to receive the therapeutic coating. Specifically, it may be determined, based at least in part on the first identifier of the of the first medical implant device, that the first medical implant device is approved to receive the therapeutic coating. This determination may include comparing the first identifier to information indicating approved identifiers of approved medical implant devices that are approved to receive therapeutic coating delivery and confirming that the first identifier is included in the approved identifiers. Referring now to FIG. 7, an example successful identifier match attempt for authorizing application of a therapeutic coating to a medical implant device will now be described in detail. In the illustrated embodiment, the reader 102 reads the first identifier 615 from the first medical implant device and provides the first identifier 615 to the computing system 104. As shown, in this example, the first identifier 615 is XYZ456. The computing system 104 may then access approved device information 600 stored in information repository 130. In the illustrated embodiment, the computing system 104 compares the first identifier 615 (XYZ456) to the approved identifiers listed in the approved device IDs column 601 to attempt to match the first identifier 615 to one of the approved device identifiers. As shown, in this example, the first identifier 615 (XYZ456) is the identifier listed in the second row of the approved device IDs column 601. Accordingly, in this example, as indicated at action 705, the computing system 104 matches the first identifier 615 (XYZ456) to an approved device identifier, and the coating applicator system is therefore switched from the locked state, in which it is prohibited from applying a therapeutic coating, to an unlocked state, in which it is permitted to apply the therapeutic coating.

A variety of techniques may be employed for switching of the coating applicator system from the locked state to the unlocked state. As described above, in one embodiment, the locked state is analogous to a powered-off state of the coating applicator system, and the unlocked state is analogous to a powered-on state of the coating applicator system. In one embodiment, the computing system 104 may switch the coating applicator system from the locked state to the unlocked state by causing power to be applied to one or more components (e.g., applicator device 107 or base unit 401) of the coating applicator system. For example, as described above, the computing system 104 may control a switch that may be opened to restrict the supply of power to the coating applicator system components or that may be closed to allow the supply of power to the coating applicator system components. In one embodiment, the computing system 104 switches the coating applicator system to an unlocked state by sending instructions to the coating applicator system to perform coating delivery or to otherwise assume the unlocked state. These instructions may take the form of an electrical pulse or signal that is sent from the controller 104 to the applicator device 107 or the base unit 401 and/or a message that is sent via a local area network (LAN) or another communications medium. As described above, in one embodiment, the components (e.g., applicator device 107 or base unit 401) of the coating applicator system may remain powered-on even when the coating applicator system is in a locked state. In one embodiment, instead of unlocking the coating applicator system by merely powering it on, the computing system 104 may unlock the coating applicator system by providing it with instructions to assume the unlocked state. In one embodiment, the computing system 104 may switch the coating applicator system to the unlocked state by sending the coating applicator system instructions to perform a coating delivery cycle or to otherwise allow coating delivery. Additionally, in one embodiment, the computing system 104 may switch the coating applicator system to the unlocked state by sending the coating applicator system instructions to assume the unlocked state, and instructions for allowing coating delivery while in the unlocked state may be stored in memory components that may optionally be included in, or otherwise accessible to, the coating applicator system.

In one embodiment, the computing system 104 determines, based at least in part on the first identifier, a selected type of the therapeutic coating that is approved for the first medical implant device, and the coating applicator system is permitted to apply only the selected type of the therapeutic coating to the first medical implant device. For example, as shown in FIG. 7, the approved device information 600 includes an approved coating type column 602, which lists an approved coating type for each approved medical implant device. As shown, the coating type listed in the second row of column 602 is Coating Type B (e.g., triclosan), thereby indicating that the first medical device is approved to receive Coating Type B (e.g., triclosan). In one embodiment, when the coating applicator system is unlocked based on the first identifier of the first medical implant device, the coating applicator system may be restricted to applying only the approved type of coating (e.g., triclosan) before it returns to the locked state. This may assist in preventing misuse, such as by helping to ensuring that the coating applicator system cannot be used to apply unapproved or unauthorized coatings to the first medical implant device.

Additionally, in one embodiment, the computing system 104 determines, based at least in part on the first identifier, a dosage amount of the therapeutic coating that is approved for the first medical implant device, and the coating applicator system is permitted to apply no more than the dosage amount of the therapeutic coating to the first medical implant device. For example, as shown in FIG. 7, the approved device information 600 also includes an approved coating dosage column 603, which lists an approved coating dosage amount for each approved medical implant device. As shown, the dosage amount listed in the second row of column 603 is 2 mL, thereby indicating that the first medical device is approved to receive 2 mL of Coating Type B (e.g., triclosan). In one embodiment, when the coating applicator system in unlocked based on the first identifier of the first medical implant device, the coating applicator system may be restricted to applying no more than (and in some cases no less than) the approved coating dosage amount (e.g., 2 mL) before it returns to the locked state. This may assist in preventing misuse, such as by helping to ensuring that the coating applicator system cannot be used to apply more than (and in some cases no less than) the approved coating dosage amount to the first medical implant device.

In one embodiment, as described with reference to FIGS. 1-3, the therapeutic coating that is applied to the first medical implant device is included in a cartridge 103 that is inserted into an applicator device 107. In one embodiment, the cartridge 103 also has a respective identifier that is read by the reader 102, such as from an identification tag that is included on the cartridge 103. This cartridge identifier may be used to determine a type and/or dosage of the therapeutic coating that is included within the cartridge 103. For example, in some cases, the computing system 104 may access stored information that indicates various cartridge identifiers and a respective type and/or dosage of the therapeutic coating for each cartridge identifier. In one embodiment, this information may also be stored in information repository 130. This information is used to confirm that the cartridge 103 includes the type and/or dosage of the therapeutic coating that has been approved for the first medical implant device. In one embodiment, in order to unlock the coating applicator system, the computing system 104 requires the cartridge identifier to be read (e.g., by an electronic reader) and requires a confirmation that the cartridge identifier indicates a type and/or dosage of the therapeutic coating that has been approved for the first medical implant device. Additionally, in one embodiment, while in the unlocked state, the coating applicator system may be permitted to only apply coating from a single cartridge before being switched back to the locked state. This may be accomplished by various techniques, such as by unlocking the coating applicator system only for a specified time period, such as based on an estimated (e.g., average) amount of time that it takes to perform device coating using a single cartridge. In this manner, the coating applicator system may be restricted to applying only the approved type of coating (e.g., triclosan) and/or to applying no more than the approved coating dosage amount (e.g., 2 mL) before it returns to the locked state.

In an alternative embodiment, as described with reference to FIG. 4, the therapeutic coating that is applied to the first medical implant device is included in a bag 402 into which the first medical implant device is inserted for application of the therapeutic coating. In one embodiment, the bag 402 also has a respective identifier that is read by the reader 102, such as from an identification tag that is included on the bag 402. This bag identifier may be used to determine a type and/or dosage of the therapeutic coating that is included within the bag 402. For example, in some cases, the computing system 104 may access stored information that indicates various bag identifiers and a respective type and/or dosage of the therapeutic coating for each bag identifier. In one embodiment, this information may also be stored in information repository 130. This information is used to confirm that the bag 402 includes the type and/or dosage of the therapeutic coating that has been approved for the first medical implant device. In one embodiment, in order to unlock the coating applicator system, the computing system requires the bag identifier to be read (e.g., by an electronic reader) and requires a confirmation that the bag identifier indicates a type and/or dosage of the therapeutic coating that has been approved for the first medical implant device. Additionally, in one embodiment, while in the unlocked state, the base unit 401 may be permitted to only interact with only a single bag 402 before being switched back to the locked state. This may be accomplished by various techniques, such as by unlocking the coating applicator system only for a specified time period, such as based on an estimated (e.g., average) amount of time that it takes to perform device coating using a single bag. In this manner, the coating applicator system may be restricted to applying only the approved type of coating (e.g., triclosan) and/or to applying no more than the approved coating dosage amount (e.g., 2 mL) before it returns to the locked state.

In some cases, the approved device information may also include additional information about the approved medical implant devices. In one embodiment, the approved device information may include information regarding coating of medical implant devices in different operating environments and/or for different patients. For example, certain types of infections may be more common in certain geographic areas, in certain operating environments (e.g., hospital vs. field clinic, etc.), at certain times of the year, and/or based on other factors. For these and other cases, the approved device information could potentially identify different types and/or dosage amounts of approved coatings under one or more of these or other different environmental conditions. Moreover, an optimal type and/or dosage of coating could also vary based on patient factors, such as gender, age, health conditions, family history, other medications being taken, and the like. The approved device information could also potentially identify different types and/or dosage amounts of approved coatings under one or more of these or other different patient conditions. In one specific example, the system could be programmed, in order to switch to the unlocked state, to prompt the user certify that the patient has no health-related issues and/or contraindications when exposed to a particular coating (e.g., triclosan). The system could prevent switching to the unlocked state if a proper certification is not provided.

In one embodiment, the system is configured to provide a warning and/or prevention of the use of incompatible medical implant devices that are inadvertently being used together, such as devices with incompatible sizes, mismatching threads, or scenarios where two right or two left devices are mistakenly used instead of a right device and a left device. For example, in some cases, the computing system may determine the types of medical implant devices that are being coated, such as based on the identifiers of the medical implant devices. For example, for each stored device identifier, the approved device information may indicate a type of device (e.g., size, left or right, etc.) to which the identifier corresponds, and this information may be accessed by the computing system. The computing system may then compare these medical device types and provide a warning (or prevent unlocking) when an attempt is made to coat incompatible device types, such as when they are being coated together or within a selected threshold time period of one another. Also, in one embodiment, when a medical implant device is implanted into a patient, information about the patient (e.g., name, gender, age, contact information, etc.) may be associated with the device identifier (and potentially an indication of the applied therapeutic coating) and stored, for example in the approved device information, a manufacturer database, a patient medical record, and the like. This may assist in tracking of the medical implant device and the patient, such as to assist in performance post-operative procedures, further information gathering, and the like.

At operation 518, the therapeutic coating is applied to the first medical implant device. The therapeutic coating is applied by the coating applicator system while in the unlocked state. In the embodiment of FIGS. 1-3, the therapeutic coating is applied from a cartridge that is inserted into an applicator device. The applicator device may cause the coating to be applied to the first medical implant device by heating the coating and lowering pressure within the interior area of the applicator device, thereby causing the coating to be delivered to the first medical implant device. In the embodiment of FIG. 4, the first medical implant device is inserted into, and enclosed within, a bag in order to apply the coating. A base unit provides an electrical connection for heating the bag. The base unit also extracts air from the bag, thereby causing a vacuum within the bag. The heating of the bag in combination with the air vacuum results in the coating being applied to the first medical implant device. Any other suitable technique for application of the therapeutic coating to the first medical implant device may also be employed.

At operation 520, the coating applicator system is switched from the unlocked state back to the locked state. The coating applicator system is switched from the unlocked state back to the locked state after the applying of the therapeutic coating to the first medical implant device. Various techniques may be employed to determine when to switch the coating applicator system from the unlocked state back to the locked state. In one embodiment, the coating applicator system is configured to perform a timed coating cycle to deliver the therapeutic coating to the first medical device. In some examples, the coating applicator system may be configured to automatically switch back to the locked state at the conclusion of this coating cycle. Alternatively, the coating applicator system may notify the computing system when the coating cycle concludes, and the computing system may then switch the coating applicator system back to the locked state. In some cases, the time period for this coating cycle may vary, for example depending upon the type of coating be applied, the coating dosage, the size and/or type of medical implant device, the application technique being used (e.g., cartridge, bag, etc.), and/or other factors. In an alternative embodiment, the coating applicator system is unlocked only for a specified time period, such as based on an estimated (e.g., average) amount of time that it takes to deliver a therapeutic coating to a medical implant device. In some examples, this estimated time period may vary, for example depending upon any or all of the factors described above. In some cases, the computing system may keep track of this time period and may switch the coating applicator system back to the locked state at the conclusion of the time period. These techniques may assist in preventing misuse, such as by helping to ensure that the coating applicator system cannot be unlocked using a single device identifier to apply multiple coatings to multiple medical implant devices.

Various techniques may be employed for switching the coating applicator system from the unlocked state back to the locked state. As described above, in one embodiment, the locked state is analogous to a powered-off state of the coating applicator system, and the unlocked state is analogous to a powered-on state of the coating applicator system. In some examples, the computing system 104 may switch the coating applicator system from the unlocked state to the locked state by powering-off one or more components (e.g., applicator device 107 or base unit 401) of the coating applicator system. For example, as described above, the computing system 104 may control a switch that may be opened to restrict the supply of power to the coating applicator system components or that may be closed to allow the supply of power to the coating applicator system components. In one embodiment, the computing system 104 switches the coating applicator system to a locked state by sending instructions to the coating applicator system to not perform coating delivery or to otherwise assume the locked state. In one embodiment, the computing system 104 may send instructions to the coating applicator system (e.g., applicator device 107 or base unit 401) to power itself off. In yet another embodiment, the coating applicator system may automatically switch itself to the locked state, such as by powering itself off, for example at the conclusion of a coating application cycle. As also described above, in an alternative embodiment, the applicator device 107, base unit 401, and/or other components of the coating applicator system may be powered-on when in the locked state, but the coating applicator system may nevertheless be prohibited from applying a therapeutic coating. In one embodiment, as opposed to powering off the coating applicator system, the computing system 104 may send instructions to the coating applicator system to prohibit the application of therapeutic coating until the coating applicator system is again switched back into the unlocked state. In one embodiment, the computing system 104 may switch the coating applicator system to the locked state by sending the coating applicator system instructions to not perform coating delivery. Additionally, in one embodiment, the computing system 104 may switch the coating applicator system to the locked state by sending the coating applicator system instructions to assume the locked state, and instructions for not allowing coating delivery while in the locked state may be stored in memory components that may optionally be included in, or otherwise accessible to, the coating applicator system.

Figure 8:
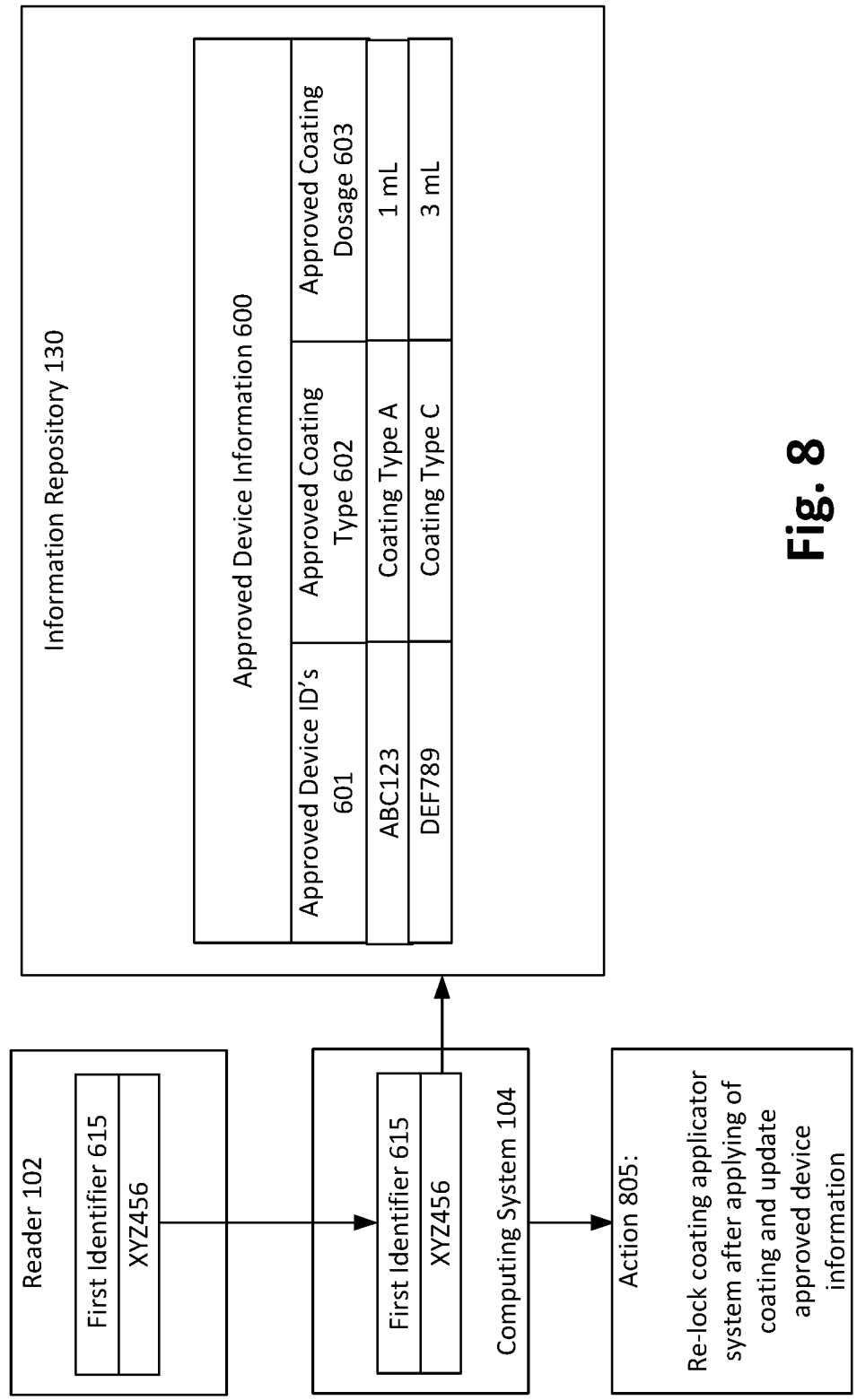
FIG. 8 is a diagram illustrating an example status information update for an identifier of a medical implant device.

At operation 522, approved device information is updated based on the applying of the therapeutic coating to the first medical implant device. Specifically, the computing system may remove the first identifier of the first medical implant device from the approved identifiers based on the applying of the therapeutic coating to the first medical implant device. For example, referring now to FIG. 8, an example is shown in which, after applying of the therapeutic coating to the first medical implant device, an action 805 is performed to relock the coating applicator system and update the approved device information 600. In the illustrated embodiment, the approved device information 600 is updated by removing first identifier 615 (XYZ456) from the approved device information 600, thereby indicating that the first medical implant device is no longer approved to receive a therapeutic coating. As shown, the identifier XYZ456 (which was included in the second row of approved device information 600 in FIG. 7) is removed from the approved device information 600 in FIG. 8. This may prevent misuse, such as by preventing the identifier XYZ456 from being reused to apply other therapeutic coatings to other devices. It is noted that the removal of the first identifier from the approved identifiers does not necessarily require any deletion of information about the first identifier. For example, in some cases, the first identifier may be removed from the approved identifiers by changing a status of the first identifier, such as from "coating not yet applied" to "coating already applied" or using any other similar designations or techniques.

Thus, the techniques described above may help to ensure that a coating applicator system is used to only apply therapeutic coatings to medical implant devices for which they are approved, thereby helping to eliminate off-label or other intentional or accidental misuse of the coating applicator system. The techniques may also help to ensure that the proper type and dosage of the therapeutic coatings are applied to the approved medical implant devices. From a regulatory perspective, these and other safeguards may allow the coating applicator system to be treated not as a drug delivery system but as a but as an instrument to produce a combination drug-device at the point-of-care. This may potentially enable a less burdensome regulatory pathway for the coating applicator system. This may allow for eased inventory management, such as by not requiring excessive stock keeping units (SKUs) for coated devices and non-coated devices.

As described above, when a medical implant device is implanted into a patient, information about the patient (e.g., name, gender, age, contact information, etc.) may be associated with the device identifier (and potentially an indication of the applied therapeutic coating) and stored, for example in the approved device information, a manufacturer database, a patient medical record, and the like. This may assist in tracking of the medical implant device and the patient, such as to assist in performance post-operative procedures, further information gathering, and the like. Moreover, it is noted that the use of an RFID tag that is embedded into a medical implant device may allow the device identifier to be read even after medical implant device is implanted into the patient. In one embodiment, the used of an embedded RFID tag acts as a key to control the use of other treatments that are applied to the patient postoperatively. For example, these may include the use of specific antibiotic treatments or other forms of bone enhancements that may be required to prevent loosening or revision of the implant.

Example Computing System

Figure 9:
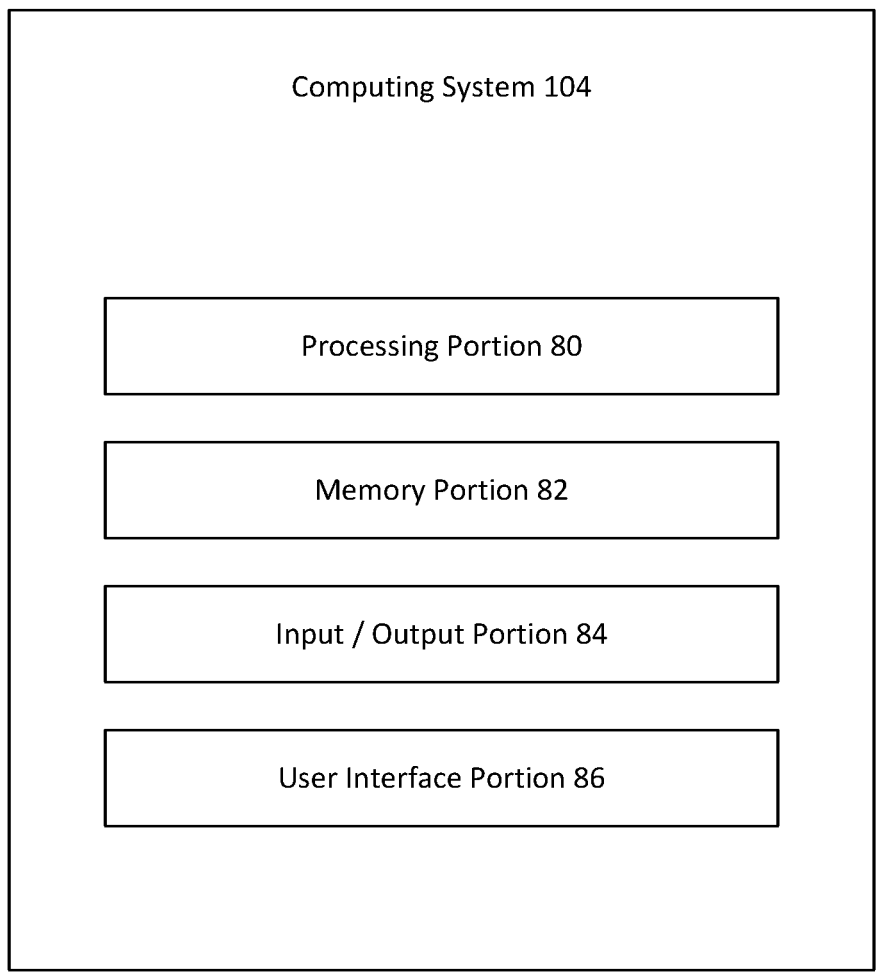
FIG. 9 is diagram of an example computing device that may be employed to perform applicator control operations described herein.

A computing system, as that term is used herein, refers to a system including at least processing components and memory components that is programmable to perform computing operations. A computing system may can include, for example, one or more of a desktop computing system, or a portable computing system, such as a laptop, tablet, or smart phone, processing, memory and other components implemented using integrated circuits, microchips, and the like. In addition to processing and memory components, a computing system may optionally include other types of components, such as input/output components and user interface components. Referring to FIG. 9, an example embodiment of computing system 104 will now be described in detail. As described above, in some examples, computing system 104 may be wholly or partially included in coating applicator system 110. Additionally, in some examples, in addition to computing system 104, coating applicator system 110 may optionally include one or more of the components shown in FIG. 9, such as any or all of processing components, memory components, input/output components, and user interface components.

In an example configuration, the computing system 104 includes a processing portion 80, a memory portion 82, an input/output portion 84, and a user interface (UI) portion 86. It is emphasized that the block diagram depiction of the computing system 104 is exemplary and not intended to imply a specific implementation and/or configuration. The processing portion 80, memory portion 82, input/output portion 84, and user interface portion 86 can be coupled together to allow communications therebetween. As should be appreciated, any of the above components may be distributed across one or more separate devices and/or locations.

In various embodiments, the input/output portion 84 includes a receiver of the computing system 104, a transmitter of the computing system 104, or a combination thereof. The input/output portion 84 is capable of receiving and/or providing information pertaining to communicating over a network such as, for example, a local area network (LAN) or a wide area network (e.g., the Internet). As should be appreciated, transmit and receive functionality may also be provided by one or more devices external to the computing system 104.

The processing portion 80 may include one or more processors. Depending upon the exact configuration and type of processor, the memory portion 82 can be volatile (such as some types of RAM), non-volatile (such as ROM, flash memory, etc.), or a combination thereof. The computing system 104 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the computing system 104.

The computing system 104 also can contain the user interface portion 86 allowing a user to communicate with the computing system 104. The user interface 86 can include inputs that provide the ability to control the computing system 104, via, for example, buttons, soft keys, a mouse, voice actuated controls, a touch screen, movement of the computing system 104, visual cues (e.g., moving a hand in front of a camera on the computing system 104), or the like. The user interface portion 86 can provide outputs, including visual information (e.g., via a display), audio information (e.g., via speaker), mechanically (e.g., via a vibrating mechanism), or a combination thereof. In various configurations, the user interface portion 86 can include a display, one or more graphical user interfaces, a touch screen, a keyboard, a mouse, an accelerometer, a motion detector, a speaker, a microphone, a camera, a tilt sensor, or any combination thereof. Thus, in one embodiment, a computing system can include a processor, a display coupled to the processor, and a memory in communication with the processor, one or more graphical user interfaces, and various other components. The memory can have stored therein instructions that, upon execution by the processor, cause the computer system to perform operations, such as the operations described above.

While example embodiments of devices for executing the disclosed techniques are described herein, the underlying concepts can be applied to any system capable of performing the techniques described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other processor-readable or machine-readable storage medium (computer-readable storage medium), wherein, when the program code is loaded into and executed by a machine, such as a computer, the machine becomes an apparatus for performing the techniques described herein. In the case of program code execution on programmable computers, the computing system will generally include a processor, a storage medium readable by the processor (including volatile and non-volatile memory and/or storage elements), and may include at least one input device, and at least one output device, for instance a display. The display can be configured to display visual information. The program(s) can be implemented in assembly or machine language, if desired. The language can be a compiled or interpreted language and combined with hardware implementations.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed is:

1. A computing system for controlling delivery of a therapeutic coating to a first medical implant device, the computing system comprising:
   one or more processors; and
   one or more memories having stored therein instructions that, upon execution by the one or more processors, cause the computing system to perform the following steps:
      receiving a first identifier of the first medical implant device;
      determining, based at least in part on the first identifier, that the first medical implant device is approved to receive the therapeutic coating, wherein the determining, based at least in part on the first identifier, that the first medical implant device is approved to receive the therapeutic coating comprises:
         comparing the first identifier to information indicating approved identifiers of approved medical implant devices that are approved to receive therapeutic coating delivery; and
         confirming that the first identifier is included in the approved identifiers;
      in response to the determining, based at least in part on the first identifier, that the first medical implant device is approved to receive the therapeutic coating, switching a coating applicator system from a locked state in which the coating applicator system is prohibited from applying the therapeutic coating to an unlocked state in which the coating applicator system is permitted to apply the therapeutic coating to the first medical implant device, wherein the coating applicator system, while in the unlocked state, applies the therapeutic coating to the first medical implant device; and removing the first identifier from the approved identifiers based on application of the therapeutic coating to the first medical implant device.

2. The computing system of claim 1, wherein the one or more memories have stored therein further instructions that, upon execution by the one or more processors, cause the computing system to perform an additional step of:
determining, based at least in part on the first identifier, a dosage amount of the therapeutic coating that is approved for the first medical implant device, wherein the coating applicator system is permitted to apply no more than the dosage amount of the therapeutic coating to the first medical implant device.

3. The computing system of claim 1, wherein the one or more memories have stored therein further instructions that, upon execution by the one or more processors, cause the computing system to perform an additional step of:
determining, based at least in part on the first identifier, a selected type of the therapeutic coating that is approved for the first medical implant device, wherein the coating applicator system is permitted to apply only the selected type of the therapeutic coating to the first medical implant device.

4. The computing system of claim 1, wherein the first identifier is received from an electronic reader that reads the first identifier.

5. The computing system of claim 4, wherein the electronic reader is a radio-frequency identification (RFID) reader.

6. The computing system of claim 4, wherein the first identifier is read from the first medical implant device.

7. The computing system of claim 1, wherein the one or more memories have stored therein further instructions that, upon execution by the one or more processors, cause the computing system to perform an additional step of:
switching, after the therapeutic coating is applied to the first medical implant device, the coating applicator system from the unlocked state back to the locked state.

8. A method for controlling delivery of a therapeutic coating to a first medical implant device, the method comprising:
receiving, by a computing system, a first identifier of the first medical implant device,
determining, by the computing system, based at least in part on the first identifier, that the first medical implant device is approved to receive the therapeutic coating, wherein the determining, based at least in part on the first identifier, that the first medical implant device is approved to receive the therapeutic coating comprises:
comparing the first identifier to information indicating approved identifiers of approved medical implant devices that are approved to receive therapeutic coating delivery; and
confirming that the first identifier is included in the approved identifiers;
in response to the determining, based at least in part on the first identifier, that the first medical implant device is approved to receive the therapeutic coating, switching, by the computing system, a coating applicator system from a locked state in which the coating applicator system is prohibited from applying the therapeutic coating to an unlocked state in which the coating applicator system is permitted to apply the therapeutic coating to the first medical implant device, wherein the coating applicator system, while in the unlocked state, applies the therapeutic coating to the first medical implant device; and removing, by the computing system, the first identifier from the approved identifiers based on application of the therapeutic coating to the first medical implant device.

9. The method of claim 8, further comprising determining, based at least in part on the first identifier, a dosage amount of the therapeutic coating that is approved for the first medical implant device, wherein the coating applicator system is permitted to apply no more than the dosage amount of the therapeutic coating to the first medical implant device.

10. The method of claim 8, further comprising determining, based at least in part on the first identifier, a selected type of the therapeutic coating that is approved for the first medical implant device, wherein the coating applicator system is permitted to apply only the selected type of the therapeutic coating to the first medical implant device.

11. The method of claim 8, further comprising switching, after the therapeutic coating is applied to the first medical implant device, the coating applicator system from the unlocked state back to the locked state.

12. The method of claim 8, further comprising reading, using an electronic reader the first identifier.

13. The method of claim 12, wherein the electronic reader is a radio-frequency identification (RFID) reader.

14. The method of claim 12, wherein the first identifier is read from the first medical implant device.

15. The method of claim 14, wherein a packaging of the first medical implant device shields the first medical implant device by preventing the reading of the first identifier from the first medical implant device while the first medical implant device is enclosed within the packaging.

16. The method of claim 12, wherein the electronic reader is included in an applicator device of the coating applicator system and is configured to read device identifiers in an interior area of the applicator device, and wherein access to the interior area of the applicator device is limited such that another medical implant device cannot be inserted into the interior area of the applicator device after the reading of the first identifier and prior to the application of the therapeutic coating to the first medical implant device.

17. The method of claim 8, wherein the coating applicator system comprises a base unit and a bag, wherein the first medical implant device is inserted into the bag, wherein the base unit provides an electrical connection for heating the bag and causes an air vacuum to occur in the bag, and wherein the heating of the bag and the air vacuum result in the application of the therapeutic coating to the first medical implant device.

18. The method of claim 8, wherein the first identifier is received via manual entry by a user.

19. The method of claim 8, further comprising sensing a physical attribute of the first medical implant device.

20. A method for controlling delivery of a therapeutic coating to a first medical implant device, the method comprising:
receiving, by a computing system, a first identifier of the first medical implant device,
determining, by the computing system, based at least in part on the first identifier, that the first medical implant device is approved to receive the therapeutic coating;
in response to the determining, based at least in part on the first identifier, that the first medical implant device is approved to receive the therapeutic coating, switching, by the computing system, a coating applicator system from a locked state in which the coating applicator system is prohibited from applying the therapeutic coating to an unlocked state in which the coating applicator system is permitted to apply the therapeutic coating to the first medical implant device, wherein the coating applicator system, while in the unlocked state, applies the therapeutic coating to the first medical implant device, wherein the coating applicator system comprises a base unit and a bag, wherein the first medical implant device is inserted into the bag, wherein the base unit provides an electrical connection for heating the bag and causes an air vacuum to occur in the bag, and wherein the heating of the bag and the air vacuum result in application of the therapeutic coating to the first medical implant device.

* * * * *